(12) United States Patent
Brinkmann

(10) Patent No.: US 8,586,060 B2
(45) Date of Patent: Nov. 19, 2013

(54) COSMETIC OR PHARMACEUTICAL PREPARATION

(75) Inventor: Bernd Brinkmann, Erkelenz (DE)

(73) Assignee: Walter Rau Neusser Oel und Fett AG, Neuss (DE)

( * ) Notice: Subject to any disclaimer, the term of this patent is extended or adjusted under 35 U.S.C. 154(b) by 994 days.

(21) Appl. No.: 12/348,057

(22) Filed: Jan. 2, 2009

(65) Prior Publication Data

US 2009/0192233 A1    Jul. 30, 2009

(51) Int. Cl.
*A61K 9/00*    (2006.01)
*A01N 47/00*    (2006.01)

(52) U.S. Cl.
USPC .......................................... 424/400; 514/786

(58) Field of Classification Search
None
See application file for complete search history.

(56) References Cited

U.S. PATENT DOCUMENTS

| | | | |
|---|---|---|---|
| 4,847,296 A * | 7/1989 | Babayan et al. | 514/552 |
| 4,996,074 A * | 2/1991 | Seiden et al. | 426/601 |
| 5,380,544 A * | 1/1995 | Klemann et al. | 426/607 |
| 6,518,226 B2 * | 2/2003 | Volker et al. | 508/485 |
| 2003/0207971 A1 | 11/2003 | Stuart, Jr. et al. | |
| 2005/0186230 A1 * | 8/2005 | Chen | 424/400 |
| 2006/0257353 A1 | 11/2006 | Jahaniaval | |

FOREIGN PATENT DOCUMENTS

| | | |
|---|---|---|
| DE | 26 54 743 | 6/1978 |
| DE | 102004010246 A1 | 9/2005 |
| DE | 102004036437 A1 | 3/2006 |
| DE | 202005019454 U1 | 7/2006 |
| DE | 102005015632 A1 | 10/2006 |
| DE | 202005019453 U1 | 12/2006 |
| DE | 102005052442 A1 | 6/2007 |
| WO | WO 00/69273 | 11/2000 |
| WO | WO 2007/103398 | 9/2007 |

* cited by examiner

*Primary Examiner* — Brian Gulledge
*Assistant Examiner* — Snigdha Maewall
(74) *Attorney, Agent, or Firm* — Collard & Roe, P.C.

(57) ABSTRACT

The invention proposes a cosmetic or pharmaceutical preparation containing a mixture of medium-chain, preferably saturated triglycerides with a fatty acid chain length of between C8 and C10 of between 60% and 98% and a content of saturated, long-chain, preferably saturated triglycerides with a fatty acid chain length of between C18 and C24 of between 2% and 40% as a vegetable replacement for Vaseline.

14 Claims, No Drawings

COSMETIC OR PHARMACEUTICAL PREPARATION

BACKGROUND OF THE INVENTION

The invention relates to a cosmetic or pharmaceutical preparation of the kind typically used in crèmes, skin lotions, lipsticks and other cosmetic end products or in pharmacy salves. In particular, the invention relates to a preparation manufactured on a purely vegetable basis intended as a replacement or substitute for the known Vaseline (petrolatum).

Vaseline is a petroleum-based product used frequently in cosmetics and pharmacies that has been generally known for some time. It is precisely in the area of cosmetics that petroleum-based constituents are often the focus of criticism due to potentially adverse properties. In particular the grooming characteristics of petroleum derivatives are much worse than those exhibited by substances especially of vegetable origin, because the molecular size of certain components in the Vaseline exceeds the pore size of human skin.

In response to this criticism, attempts have already been made to provide a vegetable-based replacement for Vaseline. German Utility Models DE 20 2005 019 453 U1 and DE 20 2005 019 454 U1 each describe vegetable-based cosmetics consisting of vegetable oils, vegetable fats, vegetable waxes and possibly beeswax, Vitamin E and fragrances, in particular ether oils. In the two aforementioned utility model specifications, in particular the following vegetable oils or fats are used for manufacturing so-called vegan Biomelk fat: canola oil, palm oil, olive oil, castor oil, jojoba oil, palm sterin, shea butter and coconut oil.

The disadvantage to the known preparation lies in the difficulty of setting the desired viscosity given the use of natural products with a typically fluctuating composition. In addition, the typical rheological properties of the Vaseline cannot be achieved to the desired extent. In particular, the shelf life of the previously known preparation is unsatisfactory; after a certain storage period, in particular at high temperatures, specific components in the previously known preparation can become rancid.

The object of the invention is to provide a vegetable-based cosmetic or pharmaceutical preparation that imitates the properties of Vaseline as effectively as possible, in particular its rheological properties, skin protection characteristics and long shelf life.

SUMMARY OF THE INVENTION

The aforementioned object is achieved according to the invention by means of a cosmetic or pharmaceutical preparation containing 60% to 98% of a mixture of medium-chain triglycerides (MCT)

2% to 40% of a mixture of long-chain triglycerides (LCT)

The content of MCT mixture preferably ranges between 70% and 95%, and the content of LCT mixture between 5% and 30%. Other components can consist in particular of oils, fats and waxes, in particular those of vegetable origin. All percentage indications in this application relate to percentage by weight (% w/w).

The MCT and LCT used according to the invention should be obtained entirely from vegetable raw materials. By definition, the medium-chain triglyceride mixture should exhibit fatty acids with chain lengths of 8 to 10 carbon atoms (C8 to C10). By contrast, the long-chain triglyceride mixture should preferably consist of fatty acids with chain lengths of C18 to C24.

In a particularly advantageous manner, the LCT mixture should exhibit a greater than 10% content of fatty acids with a chain length of carbon atoms greater than or equal to 20, more preferably greater than 40%, and even more preferably greater than 50%.

To achieve as long a shelf life as possible for the preparation according to the invention, the fatty acids in both the MCT mixture and LCT mixture must be saturated fatty acids. In the case of unsaturated fatty acids of the kind often encountered in natural oils and fats, partial or complete hydrogenation (hardening) can take place, if needed. This eliminates the danger of the preparation according to the invention becoming rancid.

The iodine number of the used oils or fats should range between 0 and 30, preferably between 0 and 2, and most preferably between 0 and 1.

It makes sense in particular that the parent material for the long-chain triglyceride mixture consist of a canola oil with a high content of erucic acid, a simple unsaturated fatty acid with 22 carbon atoms. It is here preferred to use the so-called behenic acid, which is the hardened form of erucic acid. The behenic acid glycerides lead to very advantageous hardening properties for the preparation. The behenic acid already acts as frame generator for a very good crystalline structure at very low percentages in the preparation as a whole measuring between 1% and 2.5%, preferably between approx. 2.5% and 15%.

It is here especially preferred that the behenic acid in the preparation be present in the so-called β'-form of the crystalline structure. This crystalline structure is distinguished by very fine crystals, and a resultant very high oil binding capacity. In this way, the content of LCT mixture in the preparation can be kept low. In addition, this yields the rheological property typical for Vaseline in the preparation according to the invention of the viscosity being high in the mechanically unloaded state, while it drops under a mechanical load, i.e., in particular during exposure to shear stress, making it possible to rub the preparation on the affected parts of the skin like a crème. After application, the preparation then exhibits a sufficient resistance once again, i.e., it does not run even at body temperature, which is important with respect to a plurality of cosmetic or pharmaceutical applications.

Transesterified mixtures of vegetable fats can be used for the LCT mixture within the framework of the invention, especially when a low melting point is desired. In this case, hardened or unhardened coconut oils are used. By increasing the melting point, hydrogenation results in a strong increase in viscosity.

Even if behenic acid-based triglycerides are preferred for the LCT mixtures, other vegetable oils are basically also conceivable, in particular in completely hydrated form. These also include completely hydrogenated canola oils, completely sunflower oils or completely hydrated soybean oil. The oils in question should contain high or predominant percentages of stearic acid (C18) and/or arachinic acid (C20). While the β-form of the crystalline structure is basically not as desirable as the β'-form mentioned in the above C22 fatty acids due to the coarser crystals, it can be achieved by targeted transesterification.

It is especially preferred that the MCT mixture be manufactured with coconut oil, which has a comparatively high content of caprylic acid (C8) and caprinic acid (C10). These MCT mixtures have a very high oxidation stability, since they consist exclusively of the fractionated, saturated fatty acids.

At room temperature, the content of crystallized fats (solid-fat content SCF)) of the preparation ranges between roughly 1% and 40%, preferably between 5% and 30%.

Other components can consist of waxes (in particular vegetable waxes, but also beeswax) and other oils with active properties, including ether oils, so that the use-related properties of the preparation according to the invention can be set as desired.

The preparation according to the invention is typically anhydrous. However, it can certainly also serve as the lipid phase of an emulsion, which then forms the finished cosmetic or pharmaceutical product or is used for its manufacture. Therefore, the preparation can be both an end product and semi-finished article, i.e., raw material, for further use in the cosmetics or pharmacy branch.

DETAILED DESCRIPTION OF PREFERRED EMBODIMENTS

The invention will be described in greater detail below using examples of preparations in the form of a vegetable-based Vaseline:

Example 1

The preparation consists of a mixture of 88% of an MCT mixture, which serves as the carrier oil, and 6% of an LCT mixture, which at room temperature is present in the preparation in a β'-crystalline form with fine crystals and high oil-binding capacity. In addition, the preparation contains 6% beeswax, which forms a mechanically stabile, water-insoluble layer on the skin, and hence acts as a barrier, just like classical petroleum-based Vaseline.

The MCT mixture in the exemplary preparation consists of approx. 60% C8 and 40% C10 fatty acids, and the iodine number of the MCT mixture is less than 1.

In the present case, the LCT mixture contains approx. 50% behenic acid made of hardened erucic acid-rich canola oil. The LCT mixture also contains approx. 40% stearic acid (C18), and low percentages totaling approx. 10% of other fatty acids. The crystals of the behenic acid glycerides serve as the frame for fabricating a crystalline structure for the preparation according to the invention that is very pleasant from a physiological standpoint.

The solid fat content in the anhydrous exemplary preparation measures 10% at 20° C.

Example 2

The preparation consists of a mixture of 90% of an MCT mixture, which serves as the carrier oil, and 10% of an LCT mixture, which at room temperature is present in the preparation in a β'-crystalline form with fine crystals and high oil-binding capacity.

The MCT mixture in the exemplary preparation consists of approx. 60% C8 and 40% C10 fatty acids, and the iodine number is less than 1.

In the present case, the LCT mixture contains approx. 50% behenic acid made of hardened erucic acid-rich canola oil. The LCT mixture also contains approx. 40% stearic acid (C18), and low percentages totaling approx. 10% of other fatty acids. The crystals of the behenic acid glycerides serve as the frame for fabricating a crystalline structure for the preparation according to the invention that is very pleasant form a physiological standpoint.

The solid fat content in the anhydrous exemplary preparation measures 9% at 20° C. This example reflects a commercially available Vaseline from a visual and rheological standpoint.

Alternative Recipe:

In the case of a recipe not according to the invention, the preparation consists of a mixture of 99% of an MCT mixture, which serves as the carrier oil, and 1% of an LCT mixture, which at room temperature is present in the preparation as a β'-crystalline form with fine crystals and high oil-binding capacity. The MCT mixture of the exemplary preparation consists of approx. 60% C8 and 40% C10 fatty acid, and the iodine number is less than 1.

In the present case, the LCT mixture contains approx. 50% behenic acid made of hardened erucic acid-rich canola oil. The LCT mixture also contains approx. 40% steric acid (C18), and low percentages totaling approx. 10% of other fatty acids. The crystals of the behenic acid glycerides serve as the frame for fabricating a crystalline structure.

The solid fat content in the anhydrous exemplary preparation was found to be <1% at 20° C. This sample is turbid and does not solidify, since the values fell outside the scope according to the invention.

The rheological properties were checked in all three aforementioned cases using a commercially available rheometer. The storage module G' in [Pa] was determined at 37° C. The samples were first subjected to oscillation for 5 minutes, after which the structural makeup was measured after 10 minutes (Table 1). The recipe according to the invention is characterized by rheological properties lying within the range of commercially available Vaselines. A deviation from the recipe of the preparation according to the invention results in products that are either too soft or too hard.

During storage at room temperature, the preparations described in Examples 1 and 2 were completely oxidation stable over a period of 12 months, i.e., exhibited no tendency to become rancid.

TABLE 1

| Sample | Composition | G' in [Pa] at 37° C. |
|---|---|---|
| Commercial sample 1 (supermarket) | 100% paraffins | 670 |
| Commercial sample 2 (OTC drugstore) | 100% paraffins | 1250 |
| Commercial sample 3 (prescription pharmacy) | 100% paraffins | 2800 |
| Example 1 | 88% MCT, 6% LCT, 6% beeswax | 2200 |
| Example 2 | 90% MCT, 10% LCT | 2000 |
| Recipe not according to invention | 99% MCT, 1% LCT | <10 |

While the invention has been illustrated and described as embodied in a cosmetic or pharmaceutical preparation, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and their equivalents.

What is claimed is:

1. A cosmetic or pharmaceutical preparation which can be used as a substitute for petrolatum, comprising:
   a mixture of medium-chain triglycerides in the range of 60% to 98%, and
   a mixture of long-chain triglycerides in the range of 2% to 40%,
   wherein the mixture of long-chain triglycerides as a whole has an iodine number less than 30.

2. The preparation according to claim 1, wherein the mixture of medium-chain triglycerides is 70% to 95% and the mixture of long-chain triglycerides is 5% to 30%.

3. The preparation according to claim 1, wherein the long chain triglycerides mixture exhibits a content of fatty acids with a carbon atom chain length of greater than or equal to 20 ranging between 10% and 100%.

4. The preparation according to claim 3, wherein the carbon chain length of greater than 20 ranges between 40% and 70%.

5. The preparation of claim 4, wherein the carbon chain length of greater than 20 is approximately 50%.

6. The preparation according to claim 1, wherein an overall content of behenic acid is at least 1%.

7. The preparation of claim 6, wherein the content is at least 2.5%.

8. The preparation of claim 7, wherein the content is at most 15%.

9. The preparation according to claim 6, wherein the behenic acid glyceride-containing long chain triglyceride mixture in the preparation is present in the (β'-form of the crystalline structure at room temperature.

10. The preparation according to claim 1, wherein the medium chain triglycerides mixture has a content of caprylic acid in the preparation which ranges between 50% and 65%.

11. The preparation according to claim 1, wherein the medium chain triglycerides mixture has a content of caprinic acid in the preparation ranges between 30% and 45%.

12. The preparation according to claim 1, wherein the medium chain triglycerides mixture as a whole has an iodine number less than 30.

13. The preparation according to claim 12, wherein the iodine number of the mixture of medium-chain triglycerides and/or iodine number of mixture of long-chain triglycerides is less than 2.

14. The preparation according to claim 13, wherein the iodine number of the mixture of medium-chain triglycerides and/or iodine number of mixture of long-chain triglycerides is less than 1.

* * * * *

UNITED STATES PATENT AND TRADEMARK OFFICE
CERTIFICATE OF CORRECTION

PATENT NO. : 8,586,060 B2
APPLICATION NO. : 12/348057
DATED : November 19, 2013
INVENTOR(S) : Brinkmann Page 1 of 1

It is certified that error appears in the above-identified patent and that said Letters Patent is hereby corrected as shown below:

In the Claims

Column 6, line 5 (line 3 of Claim 9) change "(β'-form" to correctly read: -- β'-form" --.

Signed and Sealed this
Eighteenth Day of March, 2014

Michelle K. Lee
*Deputy Director of the United States Patent and Trademark Office*